United States Patent [19]

Eross

[11] 4,210,174
[45] Jul. 1, 1980

[54] POSITIVE PRESSURE VALVES

[75] Inventor: Bela Eross, Bradfordwoods, Pa.

[73] Assignee: Instrumentation Industries, Inc., Pittsburgh, Pa.

[21] Appl. No.: 910,741

[22] Filed: May 30, 1978

[51] Int. Cl.² ............................................. F16K 15/06
[52] U.S. Cl. .................................... 137/528; 137/559; 251/65
[58] Field of Search ................... 137/528, 537; 251/65

[56] References Cited

U.S. PATENT DOCUMENTS

| 2,206,425 | 7/1940 | Perman | 137/537 |
| 2,646,071 | 7/1953 | Wagner | 137/528 |
| 3,331,389 | 7/1967 | Kirk | 137/537 X |
| 3,360,007 | 12/1967 | Haidek | 137/528 |

FOREIGN PATENT DOCUMENTS 1186300  4/1970 United Kingdom ..................... 251/65

Primary Examiner—Robert G. Nilson
Attorney, Agent, or Firm—Buell, Blenko & Ziesenheim

[57] ABSTRACT

A positive pressure valve is provided having a valve member with a central magnetically attracted member spaced from and coaxial with a rod like magnet, said valve member and magnet being relatively movable to adjust the magnetic attraction between them and thus the opening pressure of the valve.

6 Claims, 6 Drawing Figures

POSITIVE PRESSURE VALVES

This invention relates to positive pressure valves and more particularly to a magnetically controlled variable pressure valve for use in ventilators, anaesthesia machines, resuscitators and other inhalation therapy devices where it is desired to place a controlled pressure on a patient's lungs.

There are many situations in inhalation therapy where it is desirable to place a selected pressure on a patient's lungs. Typical of such instances are positive end expiratory pressure systems (PEEP) and continuous positive airway pressure systems (CPAP). This is desirable because a patient's lungs will in some cases fail simply from lack of exercise after prolonged periods of inhalation therapy. It is thus desirable, if not necessary, to apply pressure against the expiration of air by the patient so that the lungs must exert a force to expel air, and thus exercise the lungs. The force required must be adjustable so that it can suit the strength of the patient.

I have invented a positive pressure valve for such situations which is simple in structure and operation, which can be easily sterilized and which can be adjustable to pressures from about 0 to 20 cm. of water in very small increments.

I provide a generally cylindrical air tight housing, an inlet port in said housing, an outlet port in said housing spaced from said inlet port, an elongate magnet member in said housing extending generally axially thereof, a valve seat in said housing generally coaxial with said magnet, a valve member movable coaxially of said seat, a magnetically attracted member in said valve member coaxial with the magnetic member and adjusting means on the housing adjustably positioning the valve member relatively to the magnet member whereby the distance between the magnet member and the magnetically attracted member are selectively varied. Preferably the housing is in the form of a transparent plastic cylinder with a side arm at one end providing an inlet port and a side arm at the other end forming an outlet. One end of the cylinder is provided with a cap having a threaded opening receiving a threaded carrier with a cylindrical or rod shaped magnet. The other end of the cylinder is provided with a cap having a guide passage coaxial of the magnet. A frusto conical valve seat is provided in the cylinder intermediate the two side arms carrying a circular valve element with mating frusto conical edges and a central rod of magnetically attracted material sliding in the guide passage. The distance between the magnet and magnetically attracted material is varied by threading the magnet carrier through the opening in the end cap.

In the foregoing general description of my invention I have set out certain objects, purposes and advantages of the invention. Other objects, purposes and advantages of this invention will be apparent from a consideration of the following description and the accompanying drawings in which.

Figure 6:
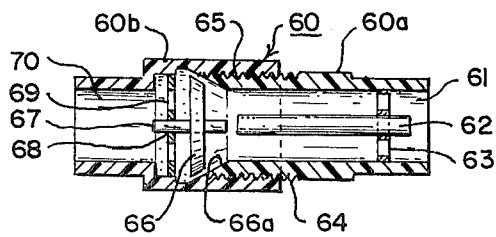
Figure 5:
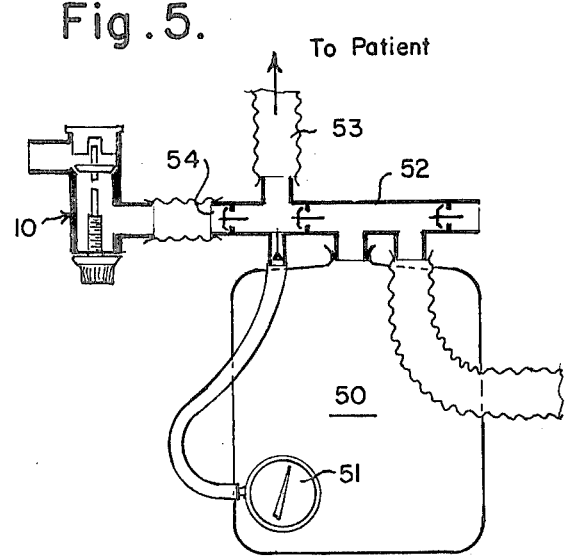

FIG. 5. is a schematic section of a continuous positive airway pressure system using the valve of this invention; and FIG. 6 is a section through a second embodiment of valve according to this invention.

Referring to the drawings, I have illustrated a valve according to this invention in the form of a cylindrical clear plastic housing 10 having side arms 11 and 12 connected thereto adjacent opposite ends and on opposite sides of housing 10. One end of housing 10 is closed by a cap 13 having a threaded opening 14 carrying a hollow threaded shaft 15 threadingly thereon. A turning knob 16 is fixed on shaft 15 outside housing 10 for rotating shaft 15. A rod magnet 17 is fixed in shaft 15. The opposite end of housing 10 is bored out to an enlarged inner diameter bore 10a to form a frusto conical seat 18, a flat circular valve element 19 having a bevel edge 20 seating on conical seat 18 is provided in the enlarged bore 10a for axial movement therein. The valve element 19 is provided with a center axial rod 21 of magnetically attracted material such as iron. A cap 22 closes said other end of housing 10 and is provided with an axial bore 23 in which rod 21 slides for guidance. The attractive force of magnet 17 on rod 21 is varied by rotating carrier 15 in and out of housing 10 by means of threads 14 in cap 13 to vary the force required to lift valve 20 from seat 18.

Figure 1:
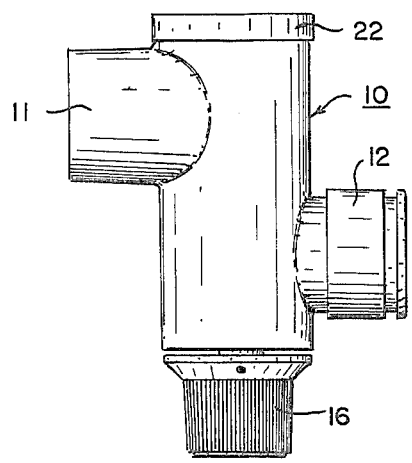
FIG. 1 is a side elevational view of a valve according to this invention.
Figure 2:
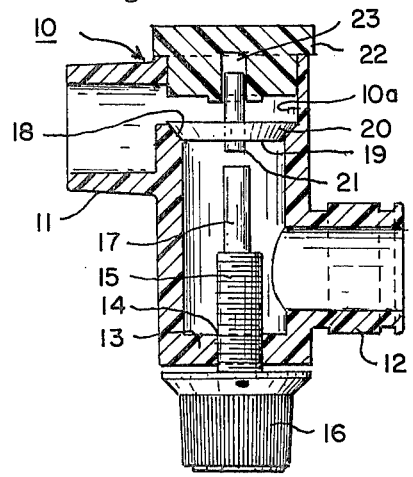
FIG. 2 is a vertical section through the valve of FIG. 1.
Figure 3:
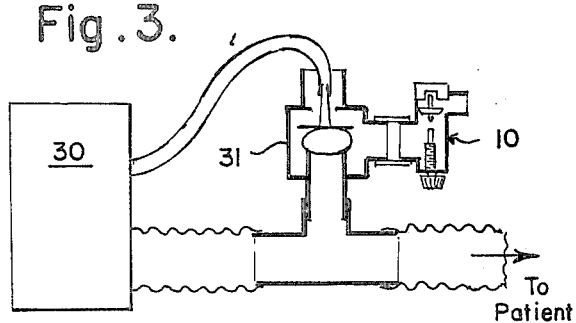
FIG. 3 is a schematic section of a standard ventilator system using the valve of FIGS. 1 and 2.
Figure 4:
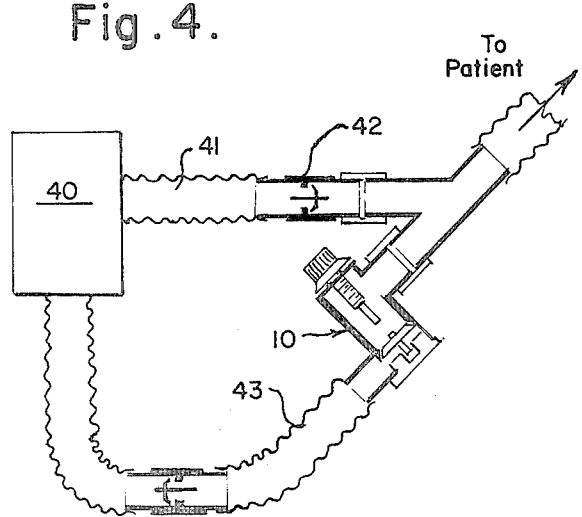
FIG. 4 is a schematic section of a circle system ventilator using the valve of this invention.

The use of the valve of FIGS. 1 and 2 in various inhalation therapy systems is illustrated in FIGS. 3 through 5. In FIG. 3 there is illustrated a standard ventilator system of ventilator 30, intermediate exhalation valve 31 and the valve of this invention connected to a patient. On inhalation the ventilator operates in normal fashion. On exhalation the exhaled air passes to the standard exhalation valve 31 and out its outlet port to the inlet side arm 12 of the valve of this invention, then through housing 10, valve 19 and out through outlet port 11. The pressure required to open valve 19 is regulated by rotating knob 16 so as to provide sufficient pressure to exercise the patient's lungs but not sufficient to cause breathing.

In the case of FIG. 4 I have illustrated a circle system ventilator of conventional construction with the valve of this invention incorporated therein. Here again, a standard circle system ventilator 40 is provided with an inspiration tube 41 and one way valve 42 going to the patient and the valve housing 10 of this invention incorporated in the return line 43.

In FIG. 5 I have illustrated a continuous positive airway pressure system of conventional design incorporating a pressure reservoir bag 50 and gauge 51 connected to a non-rebreathing valve 52 leading to an inspiration line 53 to the patient. A valve of this invention 10 is attached to the outlet 54 of non-rebreathing valve 52 to provide a regulated back pressure on the patient.

In FIG. 6 I have illustrated a second embodiment of this invention in which a cylindrical plastic housing 60 is made up of a first cylinder 60a provided with an inlet port 61 at one end and a rod magnet 62 fixed axially in said housing by radial spokes 63. The other end of said cylinder 60a is threaded 64 to receive a second larger plastic cylinder 60b threaded at one end 65 to engage the threads 64. The threaded end 64 of cylinder 60a and threaded end 65 of cylinder 60b are each formed with an internal frusto conical seat 66a receiving a circular valve member 66 carrying an axial rod of magnetically attractive material 67. The rod 67 is axially movable in a hole 68 in the center of a spider 69 carried in cylinder 60b intermediate its ends. The end of cylinder 60b opposite the threads 65 is provided with an outlet port 70. The operation of this embodiment is essentially the same as that of FIGS. 1 and 2, however, the position of valve 66 and its axial magnetically attractable member is regulated by threading the cylinder 60b on cylinder 60a so as to move the seat 66a of cylinder 60b toward or away from magnet rod 62.

In the foregoing specification, I have set out certain preferred practices and embodiments of this, however, it will be understood that this invention may be otherwise embodied within the scope of the following claims.

I claim:

1. A positive pressure valve for inhalation therapy devices comprising a generally cylindrical air tight housing, spaced apart inlet and outlet ports in said housing, an elongate magnet member in said housing extending generally axially thereof, a valve seat in said housing between said inlet and outlet ports generally coaxially of said housing, a valve member movable coaxially of said seat and housing, a magnetically attracted member in said valve member coaxial with the magnet member and adjusting means on the housing acting to adjustably position the valve member relative to the magnet member whereby the distance between the magnet member and the magnetically attracted member are selectively varied, said inlet and outlet ports being side arms extending radially from said housing adjacent opposite ends of said housing, the ends of said housing being closed by caps, one of said caps having an axially movable carrier carrying the rod-shaped magnet, the other of said caps having guide means acting on the magnetically attracted material to maintain it generally axially of the housing.

2. A positive pressure valve as claimed in claim 1 wherein the magnetically attracted material is a metallic rod coaxial of the valve member.

3. A positive pressure valve as claimed in claim 1 wherein the carrier is threadingly engaged in said one cap.

4. A positive pressure valve for inhalation therapy devices comprising a generally cylindrical air tight housing, spaced apart inlet and outlet ports in said housing, an elongate magnet member in said housing extending generally axially thereof, a valve seat in said housing between said inlet and outlet ports generally coaxially of said housing, a valve member movable coaxially of said seat and housing, a magnetically attracted member in said valve member coaxial with the magnet member and adjusting means on the housing acting to adjustably position the valve member relative to the magnet member whereby the distance between the magnet member and the magnetically attracted member are selectively varied and wherein the inlet and outlet ports are the ends of the said housing, said housing being two relatively movable cylindrical segments, one carrying the rod-like magnet and the other carrying the valve seat whereby relative movement of the two housing segments moves the rod-like magnet and the valve seat relative to one another.

5. A positive pressure valve as claimed in claim 4 wherein the two housing segments are threadingly engaged with one another for relative movement.

6. A positive pressure valve as claimed in claim 4 wherein the rod like magnet is carried fixedly in a perforate spider in one segment of said housing and the valve member has a coaxial rod like magnetically attracted member coaxial therewith and movable in a perforate spider in the other segment of said housing.

* * * * *

UNITED STATES PATENT AND TRADEMARK OFFICE
CERTIFICATE OF CORRECTION

PATENT NO. : 4,210,174

DATED : July 1, 1980

INVENTOR(S) : BELA EROSS

It is certified that error appears in the above-identified patent and that said Letters Patent are hereby corrected as shown below:

Column 2, line 41, --labored-- should be inserted before "breathing".

Signed and Sealed this

Fourth Day of November 1980

[SEAL]

Attest:

SIDNEY A. DIAMOND

Attesting Officer

Commissioner of Patents and Trademarks